United States Patent [19]

Threlkel

[11] Patent Number: 4,482,735

[45] Date of Patent: Nov. 13, 1984

[54] PROCESS FOR PREPARATION OF METHYL METHOXYACETATE

[75] Inventor: Richard S. Threlkel, El Cerrito, Calif.

[73] Assignee: Chevron Research Company, San Francisco, Calif.

[21] Appl. No.: 537,183

[22] Filed: Sep. 29, 1983

[51] Int. Cl.$^3$ ............................................. C07C 69/708
[52] U.S. Cl. ................................... 560/187; 502/201; 502/224; 502/225; 502/229; 502/230
[58] Field of Search ................... 560/187; 562/519; 502/201, 224, 225, 229, 230

[56] References Cited

U.S. PATENT DOCUMENTS

| | | | |
|---|---|---|---|
| 3,634,495 | 1/1972 | Kwantes et al. | 562/519 |
| 3,948,977 | 4/1976 | Suzuki | 560/185 |
| 3,948,986 | 4/1976 | Suzuki | 560/187 |
| 4,308,397 | 12/1981 | Suzuki | 560/187 |
| 4,356,320 | 10/1982 | Naglieri et al. | 562/519 |

FOREIGN PATENT DOCUMENTS 2063265  6/1981  United Kingdom ................ 562/519

*Primary Examiner*—Natalie Trousof
*Assistant Examiner*—Bruce D. Gray
*Attorney, Agent, or Firm*—S. R. LaPaglia; T. G. DeJonghe; C. J. Caroli

[57] ABSTRACT

A process for the preparation of methyl methoxyacetate by the oxycarbonylation of methanol which comprises reacting methanol with carbon monoxide in the presence of a hydrogen fluoride catalyst and an oxidizing agent containing a metal salt.

11 Claims, No Drawings

PROCESS FOR PREPARATION OF METHYL METHOXYACETATE

BACKGROUND OF THE INVENTION

The present invention relates to a process for the preparation of methyl methoxyacetate. More particularly, the present invention relates to the oxycarbonylation of methanol to methyl methoxyacetate by a process which comprises reacting methanol with carbon monoxide in the presence of a hydrogen fluoride catalyst and an oxidizing agent containing a metal salt.

U.S. Pat. No. 3,948,977 discloses a process for the preparation of alkoxyacetic acid and alkyl alkoxyacetate by contacting carbon monoxide with formaldehyde, an alcohol and a hydrogen fluoride catalyst.

Methyl methoxyacetate and the corresponding methoxyacetic acid are useful as solvents and as intermediates for the production of ethylene glycol ethers.

SUMMARY OF THE INVENTION

The present invention provides a process for the preparation of methyl methoxyacetate which comprises reacting methanol with carbon monoxide in the presence of a hydrogen fluoride catalyst and an oxidizing agent comprising (1) at least a stoichiometric amount of a cobalt (III) salt; or (2) a catalytic amount of a Group IB, Group VIIB or Group VIII metal salt and at least a stoichiometric amount of nitric acid or hydrogen peroxide, at a temperature in the range of about −80° C. to 120° C. and a carbon monoxide partial pressure in the range of about 5 to 5,000 psig.

Among other factors, the present invention is based on my discovery that methyl methoxyacetate can be successfully prepared by the oxycarbonylation of methanol using a hydrogen fluoride catalyst and an oxidizing agent containing a metal salt. Advantageously, the present process does not require formaldehyde, thus eliminating a step in the overall conversion of methanol to the methoxy ester.

DETAILED DESCRIPTION OF THE INVENTION

The oxidizing agents suitable for use in the process of the present invention comprise (1) at least a stoichiometric amount of a cobalt (III) salt; or (2) a catalytic amount of a Group IB, Group VIIB, or Group VIII metal salt in combination with at least a stoichiometric amount of nitric acid or hydrogen peroxide. Suitable metals include the Group IB metals, copper, silver and gold; the Group VII B metals, manganese, technetium and rhenium; and the Group VIII metals, iron, cobalt, nickel, ruthenium, rhodium, palladium, osmium, iridium and platinum. Preferred metals include manganese, cobalt and copper. An especialy preferred metal is cobalt. Typical metal salts include the fluorides, nitrates and oxides. Preferred metal salts are the fluorides, particularly, cobalt trifluoride ($CoF_3$) and cobalt difluoride ($CoF_2$). Preferred oxidizing agents include cobalt trifluoride alone, and the combinations of cobalt difluoride and nitric acid or hydrogen peroxide. An especially preferred oxidizing system is cobalt difluoride in combination with nitric acid.

The reaction may be carried out in an autoclave or any other high-pressure reactor. A general procedure is to charge the methanol, hydrogen fluoride catalyst and oxidizing agent into the reactor vessel, introduce the proper amount of carbon monoxide to obtain the desired reaction pressure and then heat the mixture at the desired temperature for the appropriate period. The reaction can be carried out batchwise or as a continuous process and the order of addition of the reactants may be varied to suit the particular apparatus employed. When the reaction is carried out in continuous form, it is preferred to use as the oxidizing agent a catalytic amount of the metal salt in combination with nitric acid or hydrogen peroxide. The reaction products are recovered and treated by any conventional method, such as distillation and/or filtration, to effect separation of the methoxy ester from unreacted materials, catalyst, oxidant, byproducts, and the like.

When the oxidizing agent comprises a cobalt (III) salt in at least stoichiometric amounts, the reactants are preferably fed to the reactor at a mole ratio of 1:2 to 20:1, methanol to cobalt (III) salt. The hydrogen fluoride should exceed 50 weight percent of the reaction solution.

When the oxidizing agent comprises a catalytic amount of a Group IB, VIIB or VIII metal salt in combination with at least a stoichiometric amount of nitric acid or hydrogen peroxide, the reactants are preferably fed to the reactor at a mole ratio of 10:1 to 1:10 of methanol to nitric acid or hydrogen peroxide, with a catalyst to oxidant mole ratio of from 1:2 to 1:1,000 of metal salt to nitric acid or hydrogen peroxide. The hydrogen fluoride should exceed 50 weight percent of the reaction solution.

As indicated above, the reaction can be suitably perfomed by introducing the carbon monoxide at a desired pressure into contact with the reaction medium containing the methanol, hydrogen fluoride and oxidant and heating to the desired temperature. In general, carbon monoxide partial pressures in the range of about 5 to 5,000 psig, preferably about 100 to 1,500 psig, may be employed. The reaction will proceed at temperatures in the range of about −80° C. to 120° C. It is generally preferred to operate the process at temperatures in the range of about −20° C. to 25° C. in order to obtain maximum selectivity. Heating and/or cooling means may be employed interior and/or exterior to the reaction to maintain the temperature within the desired range.

The reaction time is generally dependent upon the temperature, pressure and amount of catalyst and oxidant being charged, as well as the type of equipment being employed. Reaction times will vary dependent on whether the process is continuous or batch. The reaction is limited by the available oxidant, alcohol and carbon monoxide.

The following examples are provided to illustrate the invention in accordance with the principles of this invention but are not to be construed as limiting the invention in any way except as indicated by the appended claims.

EXAMPLES

EXAMPLE 1

A 300-ml magnetically-stirred stainless steel autoclave was charged with 3.0 g of $CoF_3$, 50 g of hydrogen fluoride, and 30 psi of $BF_3$ at 0° C. The autoclave was next charged to 1000 psi of carbon monoxide. 15 mls of methanol were then added to the autoclave to initiate the reaction. The autoclave was allowed to warm to 20° C. After two hours, analysis of the reaction mixture by vapor-phase chromatography showed a 53% yield of methyl methoxy acetate based on $CoF_3$.

This example illustrates the process of the present invention in which methanol and carbon monoxide are converted to methyl methoxy acetate in hydrogen fluoride/$BF_3$ solution.

EXAMPLE 2

A 300-ml magnetically-stirred stainless steel autoclave was charged with 3.0 g of $CoF_2$, 50 g of hydrogen fluoride and 30 psi of $BF_3$ at 0° C. 23 Grams of methanol were then added to the reaction solution and 1100 psi of CO was charged to the autoclave. The reaction was initiated by the addition of 5 mls of 30% hydrogen peroxide. The autoclave was warmed to 20° C. After 7 hours analysis of the reaction solution by vapor-phase chromatography showed a 16% yield of methyl methoxy acetate based on hydrogen peroxide.

EXAMPLE 3

The same procedure was followed as in Example 2 except that 5.1 grams of $MnF_3$ were used in place of $CoF_2$. The yield of methyl methoxy acetate was 10% based on hydrogen peroxide.

EXAMPLE 4

The same procedure was followed as in Example 2 except that 5.0 grams of $Cu_2O$ were used instead of $CoF_2$. The yield of methyl methoxy acetate was 8% based on hydrogen peroxide.

EXAMPLE 5

A 300-ml magnetically-stirred stainless steel autoclave was charged with 1.0 g of $CoF_2$, 10 g of methanol, and 50 g of hydrogen fluoride at 0° C. The autoclave was charged with 900 psi of carbon monoxide. Five grams of 70% nitric acid were added to initiate the reaction. After stirring at 20° C. for 2 days, analysis of products by vapor-phase chromatography indicated a 39% yield of methyl methoxy acetate based on nitric acid.

What is claimed is:

1. A process for the preparation of methyl methoxyacetate which comprises reacting methanol with carbon monoxide in the absence of formaldehyde and in the presence of a hydrogen fluoride catalyst and an oxidizing agent comprising
    (1) at least a stoichiometric amount of a cobalt (III) salt; or
    (2) a catalytic amount of a Group IB, Group VIIB or Group VIII metal salt and at least a stoichiometric amount of nitric acid or hydrogen peroxide, at a temperature in the range of about −80° C. to 120° C. and a carbon monoxide partial pressure in the range of about 5 to 5,000 psig.

2. The process according to claim 1, wherein the metal salt is a salt of manganese, cobalt or copper.

3. The process according to claim 2, wherein the metal salt is a salt of cobalt.

4. The process according to claim 1, wherein the metal salt is a fluoride salt.

5. The process according to claim 1, wherein the oxidizing agent is cobalt trifluoride.

6. The process according to claim 1, wherein the oxidizing agent is cobalt difluoride and nitric acid.

7. The process according to claim 1, wherein the oxidizing agent is cobalt difluoride and hydrogen peroxide.

8. The process according to claim 1, wherein the reaction is carried out at a temperature in the range of about −20° C. to 25° C.

9. The process according to claim 1, wherein the carbon monoxide partial pressure is in the range of about 100 psig to 1,500 psig.

10. The process according to claim 1, wherein the oxidizing agent is a cobalt (III) salt, and the reactants are fed to the reactor at a mole ratio of 1:2 to 20:1 methanol to cobalt (III) salt.

11. The process according to claim 1, wherein the oxidizing agent is a Group IB, VIIB or VIII metal salt and nitric acid or hydrogen peroxide, and the reactants are fed to the reactor at a mole ratio of 10:1 to 1:10, methanol to nitric acid or hydrogen peroxide, and a mole ratio of 1:2 to 1:1,000, metal salt to nitric acid or hydrogen peroxide.

* * * * *